United States Patent
Schmoll (10) Patent No.: US 9,814,384 B2
(45) Date of Patent: Nov. 14, 2017

(54) HIGH TEMPORAL RESOLUTION DOPPLER OCT IMAGING OF RETINAL BLOOD FLOW

(71) Applicant: CARL ZEISS MEDITEC AG, Jena (DE)

(72) Inventor: Tilman Schmoll, Dublin, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 0 days.

(21) Appl. No.: 15/021,770

(22) PCT Filed: Sep. 26, 2014

(86) PCT No.: PCT/EP2014/070644
§ 371 (c)(1),
(2) Date: Mar. 14, 2016

(87) PCT Pub. No.: WO2015/044366
PCT Pub. Date: Apr. 2, 2015

(65) Prior Publication Data
US 2016/0220112 A1 Aug. 4, 2016

Related U.S. Application Data

(60) Provisional application No. 61/884,515, filed on Sep. 30, 2013.

(51) Int. Cl.
*A61B 3/12* (2006.01)
*A61B 3/00* (2006.01)
(Continued)

(52) U.S. Cl.
CPC .......... *A61B 3/1233* (2013.01); *A61B 3/0025* (2013.01); *A61B 3/0041* (2013.01);
(Continued)

(58) Field of Classification Search
CPC ....... A61B 3/00; A61B 3/0025; A61B 3/0041; A61B 3/10; A61B 3/102; A61B 3/1025;
(Continued)

(56) References Cited

U.S. PATENT DOCUMENTS 6,325,512 B1 12/2001 Wei
6,726,325 B2 4/2004 Xie et al.
(Continued)

FOREIGN PATENT DOCUMENTS

WO 2006/078802 A1 7/2006
WO 2008/124845 A2 10/2008

OTHER PUBLICATIONS

An et al., "In Vivo Volumetric Imaging of Vascular Perfusion within Human Retina and Choroids with Optical Micro-Angiography", Optics Express, vol. 16, No. 15, Jul. 21, 2008, pp. 11438-11452.
(Continued)

*Primary Examiner* — Loha Ben
(74) *Attorney, Agent, or Firm* — Morrison & Foerster LLP (57) ABSTRACT

Techniques are introduced to improve the ability of OCT to determine more accurately the nature of the flow of fluids in the eye, including faster measurements of the flow and a method to reduce geometric uncertainties due to eye movements.

17 Claims, 6 Drawing Sheets

(51) Int. Cl.
  *A61B 3/10* (2006.01)
  *A61B 3/14* (2006.01)
  *A61B 5/00* (2006.01)
  *A61B 5/026* (2006.01)
  *G01B 9/02* (2006.01)

(52) U.S. Cl.
  CPC ............ *A61B 3/102* (2013.01); *A61B 3/1241* (2013.01); *A61B 3/14* (2013.01); *A61B 5/0066* (2013.01); *A61B 5/026* (2013.01); *A61B 5/7257* (2013.01); *G01B 9/02045* (2013.01); *G01B 9/02091* (2013.01); *G06T 2207/10072* (2013.01); *G06T 2207/10084* (2013.01); *G06T 2207/10101* (2013.01)

(58) Field of Classification Search
  CPC ....... A61B 3/1233; A61B 3/1241; A61B 3/12; A61B 3/14; A61B 5/0066; A61B 5/026; A61B 5/0261; A61B 5/0059; A61B 5/7257; A61B 5/743; G01B 9/0201; G01B 9/02045; G01B 9/02091; G06T 2207/10072; G06T 2207/10084
  USPC ........ 351/205, 206, 209, 246; 356/450, 477, 356/479, 484, 485, 489, 496, 497, 508, 356/512
  See application file for complete search history.

(56) References Cited

U.S. PATENT DOCUMENTS

| | | | |
|---|---|---|---|
| 7,346,770 B2* | 3/2008 | Swander | H04L 63/0464 709/201 |
| 7,359,062 B2* | 4/2008 | Chen | A61B 5/0066 356/479 |
| 7,364,296 B2* | 4/2008 | Miller | A61B 3/102 351/206 |
| 7,365,856 B2 | 4/2008 | Everett et al. | |
| 7,884,945 B2 | 2/2011 | Srinivasan et al. | |
| 8,180,131 B2 | 5/2012 | Toth et al. | |
| 8,244,334 B2* | 8/2012 | Huang | A61B 3/102 600/476 |
| 9,046,339 B2* | 6/2015 | Blatter | G01B 9/02091 |
| 9,192,294 B2* | 11/2015 | Sharma | A61B 3/102 |
| 9,357,916 B2* | 6/2016 | Srivastava | G01B 9/02083 |
| 9,492,082 B2* | 11/2016 | Yoshida | A61B 5/0066 |
| 2007/0291277 A1 | 12/2007 | Everett et al. | |
| 2011/0267340 A1 | 11/2011 | Kraus et al. | |
| 2012/0249956 A1 | 10/2012 | Narasimha-Iyer et al. | |
| 2014/0276025 A1 | 9/2014 | Durbin et al. | |

OTHER PUBLICATIONS

Bernardes et al., "Digital Ocular Fundus Imaging: A Review", Ophthalmologica, vol. 226, No. 4, 2011, pp. 161-181.

Chen et al., "Doppler Optical Coherence Tomography", Optical Coherence Tomography, 2008, pp. 621-651.

Ferguson et al., "Tracking Optical Coherence Tomography", Optics Letters, vol. 29, No. 18, Sep. 15, 2004, pp. 2139-2141.

Huang et al., "Optical Coherence Tomography", Science, vol. 254, No. 5035, Nov. 22, 1991, pp. 1178-1181.

Liu et al., "A Comparison of Doppler Optical Coherence Tomography Methods", Biomedical Optics Express, vol. 3, No. 10, 2012, pp. 2669-2680.

Michaely et al., "Vectorial Reconstruction of Retinal Blood flow in Three Dimensions measured with High Resolution Resonant Doppler Fourier domain Optical Coherence Tomography", Journal of Biomedical Optics, vol. 12, No. 4, Jul./Aug. 2007, pp. 041213-1-041213-7.

Park et al., "Real-Time Fiber-Based Multi-Functional Spectral-Domain Optical Coherence Tomography at 1.3 µm", Optics Express, vol. 13, No. 11, May 30, 2005, pp. 3931-3944.

International Preliminary Report on Patentability received for PCT Patent Application No. PCT/EP2014/070644, dated Apr. 14, 2016, 11 pages.

International Search Report and Written Opinion received for PCT Patent Application No. PCT/EP2014/070644, dated Mar. 6, 2015, 14 pages.

Ren et al., "Imaging and Quantifying Transverse Flow Velocity with the Doppler bandwidth in a Phase-Resolved Functional Optical Coherence Tomography", Optics Letters, vol. 27, No. 6, Mar. 15, 2002, pp. 409-411.

Singh et al., "Stable Absolute Flow Estimation with Doppler OCT based on Virtual Circumpapillary Scans", Biomedical Optics Express, vol. 1, No. 4, Nov. 2010, pp. 1047-1059.

Srinivasan et al., "High-Definition and 3-Dimensional Imaging of Macular Pathologies with High-Speed Ultrahigh-Resolution Optical Coherence Tomography", Ophthalmology, vol. 113, No. 11, Nov. 2006, pp. 2054.e1-2054.e14.

Szkulmowska et al., "Three-Dimensional Quantitative Imaging of Retinal and Choroidal Blood Flow Velocity using Joint Spectral and Time Domain Optical Coherence Tomography", Optics Express, vol. 17, No. 13, Jun. 2009, pp. 10584-10598.

Tan et al., "Doppler Optical Coherence Tomography of Retinal Circulation", Journal of Visualized Experiments, vol. 67, Sep. 2012, 6 pages.

Wang et al., "Autocorrelation Optical Coherence Tomography for Mapping Transverse Particle-Flow Velocity", Optical Letters, vol. 35, No. 21, Nov. 1, 2010, pp. 3538-3540.

Wang et al., "Doppler Optical Micro-Angiography for Volumetric imaging of Vascular Perfusion in Vivo", Optics Express, vol. 17, Issue 11, May 2009, pp. 8926-8940.

Wang et al., "In Vivo Total Retinal Blood Flow Measurement by Fourier Domain Doppler Optical Coherence Tomography", Journal of Biomedical Optics, vol. 12, No. 4, Jul./Aug. 2007, pp. 041215-1-041215-8.

Wang et al., "Retinal Blood Flow Measurement by Circumpapillary Fourier Domain Doppler Optical Coherence Tomography", Journal of Biomedical Optics, vol. 13, No. 6, Nov./Dec. 2008, pp. 064003-1-064003-9.

Zhao et al., "Doppler Standard Deviation Imaging for Clinical Monitoring of in Vivo Human Skin Blood Flow", Optics Express, vol. 25, No. 18, Sep. 15, 2000, pp. 1358-1360.

* cited by examiner

HIGH TEMPORAL RESOLUTION DOPPLER OCT IMAGING OF RETINAL BLOOD FLOW

CROSS-REFERENCE TO RELATED APPLICATIONS

This application is a National Phase application under 35 U.S.C. §371 of International Application No. PCT/EP2014/070644, filed Sep. 26, 2014, which claims priority to U.S. Provisional Patent Application No. 61/884,515, filed Sep. 30, 2013, the disclosure of each of which is hereby incorporated herein by reference in its entirety.

FIELD OF THE INVENTION

The present application concerns Doppler optical coherence tomography and the improvement in the accuracy of measuring blood flow in the retina.

BACKGROUND

Optical Coherence Tomography (OCT) is a technique for performing high-resolution cross-sectional imaging that can provide images of tissue structure on the micron scale in situ and in real time (see, e.g., Huang et al. 1991). OCT is a method of interferometry that determines the scattering profile of a sample along the OCT beam. Each scattering profile in the depth direction (z) is called an axial scan, or A-scan. Cross-sectional images (B-scans), and by extension 3D volumes, are built up from many A-scans, with the OCT beam moved to a set of transverse (x and y) locations on the sample. One of the principle advantages of OCT is its ability to image the various layers of the retina of the eye. Technical improvements in this modality permit data sets to be obtained in very short times. Doppler OCT can be used to determine flow velocity by measuring phase shifts between temporally separated measurements.

The ability to measure total retinal blood flow can provide an important diagnosis between healthy and pathological retinal tissue. Doppler OCT is applicable to the measurement of blood flow in the retina and in retinal vascular perfusion. The optimum area to measure total ocular blood flow is centered on the optical nerve head, as this is where most vessels enter and exit the retina. It is the current state of technology that even fast OCT systems have a difficulty acquiring temporally densely-sampled blood flow data of these vessels.

Important to proper determination of blood flow or velocities is knowledge of the angle or angular orientation between the vessel (or blood flow) and that of the beam probing the vessel (the Doppler angle). If these directions are perpendicular, then Doppler techniques, as historically practiced, yield no measurable shift. In cases where the Doppler angle is close to 90 degrees, accurate knowledge of the Doppler angle is critical to proper velocity determinations, because the absolute velocity is proportional to 1/cosine of the Doppler angle. There are, however, different OCT velocity measurement methods, using either phase or intensity variation measurements, which are influenced differently by the geometric arrangement between blood flow vector and the probe beam direction.

Doppler OCT has been successfully utilized in ophthalmologic diagnostic investigations as well as in functional imaging. (For a general introductory reference to Doppler OCT, see, e.g., Chen & Zhang 2008.) The recent advances in Fourier-domain OCT sensitivity and speed have been remarkable and have impacted the capabilities of Doppler OCT measurement capacity. The results can, however, be limited by various physical and technical reasons, such as phase de-correlation due to high velocity, Brownian motion of the fluid itself, phase wrapping, large or poorly determined Doppler angles, inappropriate scan timescales, and low spatial sampling as will be described in more detail below.

There are a variety of measurements that can obtain a frequency shift. Most of these involve measurement of phases or phase differences between normally adjacent A-scans and/or intensity or amplitude information or combinations of these various observables. There are sensitivity variations amongst these techniques, dependent upon the aforementioned geometric configuration, minimum and maximum velocities to be measured, temporal and spatial sampling, as well as variations in resolution and contrast. Other techniques used to determine a frequency shift include speckle variance, logarithmic intensity variance, differential logarithmic intensity variance, 2D correlation mapping, split spectra amplitude de-correlation, and filtering of the original fringe data. A popular technique, known as Doppler variance, uses autocorrelation which involves complex OCT data at each location (see, e.g., Zhao et al. 2000).

Circumpapillary Doppler OCT scans have been employed to provide quantitative information about the total retinal blood flow in vivo (see, e.g., Tan et al. 2012). They have typically used two concentric circular scans and determined a vessel's angle by measuring the position of its cross-section at two separate positions or locations. The drawback to this approach is that the centers of the vessel cross-sections for the two interleaved circular scans with different diameters have to be precisely detected within each individual scan. This is time consuming, especially as there has not been an automated method introduced so far. Furthermore, it is often difficult to define the center of the vessel cross-sections, leading to inaccuracies in the determination of the vessel's orientation relative to the scan or probing beam. This is of interest as small changes in this orientation with angles approaching orthogonality (in certain measurement styles) may lead to very large differences in blood flow.

The temporal resolution of the scans is limited by two factors. On the one hand, the sampling of the circumpapillary scan has to be sufficiently dense in order to avoid phase de-correlation. On the other hand, one may not arbitrarily increase the A-scan rate as this reduces the sensitivity for lower flow speeds.

Some of the Constraining Factors of Doppler OCT are Outlined Below:

Phase Noise:

The phase noise limits the minimum quantifiable velocity. It is limited by two factors, the signal to noise ratio (SNR) and the oversampling factor. The SNR limited phase noise of an OCT system is described by (Park et al. 2005):

$$\Phi_{err_{SNR}} = \frac{1}{\sqrt{SNR}}.$$

In most cases, the phase noise is limited by the oversampling of the scanning system. Ideally, the two measurements used to calculate the phase difference should be taken at the exact same location. In practice, one often uses scanning patterns, which don't allow 100% overlap between the two measurements. This causes phase de-correlation between the two measurements and, therefore, an increase in phase noise. The phase noise limited by the sampling density is described by (Park et al. 2005):

$$\Phi_{err_{sampling}} = \sqrt{\frac{4\pi}{3}\left(1 - \exp\left(-2\left(\frac{\Delta x}{d}\right)^2\right)\right)},$$

where $\Delta x$ denotes the lateral distance between two measurements, and d the $1/e^2$ beam width at the focus. Besides the scanning pattern, sample motion may significantly contribute to the phase noise in a similar fashion.

Time Difference Between Two Measurements:

The time between the two measurements used to calculate the phase difference influences the quantifiable velocity range. Larger time differences enable the detection of slower velocities, smaller time differences on the other hand shift the detectable velocity range towards higher speeds.

Fringe Wash-Out:

Fringe wash-out is mainly a problem of spectral domain OCT (SD-OCT). The phase shift introduced by moving scatterers during the integration time of the camera, causes a blurring of the interference fringe signal. This wash-out causes a reduction in the interference fringe amplitude and therefore a reduction of SNR of the signal from moving scatterers. The fringe wash-out scales with the magnitude of the phase shift. For high velocities, the fringe wash-out may be so strong, that the SNR (signal-to-noise ratio) drops below one. Since as mentioned above, the phase noise is also limited by the SNR, this is a significant problem for Doppler OCT measurements.

Doppler Angle:

Doppler OCT is only sensitive to axial motion. In order to determine the absolute velocity of a moving scatterer, it is essential to know the angle between its velocity vector and the probing beam. A precise angle determination is paramount due to the secant term in the expression for velocity from phase shift (see, e.g., Chen & Zhang 2008 review article, op. cit.). Since most of the vessels in the inner retina lie almost perpendicular to the probing beam, already small errors in the Doppler angle may significantly influence the resulting absolute velocity measurement.

SUMMARY

Many of the aforementioned problems with Doppler OCT can be reduced or even overcome if the scan timescales can be made shorter. One embodiment of the present application presents a technique to enhance the temporal resolution of measuring circumpapillary Doppler optical coherence tomography (OCT) scans. The OCT beam would be moved faster over those parts where no data are to be collected relative to the areas of interest where OCT are to be obtained. This can be achieved by scanning those areas that are known to contain principally blood vessels or other areas of interest and doing so via a dynamically or adaptively determined, real-time adjusted scan pattern, thus increasing the effective temporal resolution. Because no or very limited time is spent scanning between the vessels, the temporal resolution of the scan is improved, i.e., is finer.

In a four millimeter diameter circular scan, only about 10-20% of the A-scans are actually sampling a blood vessel, while 80-90% of the A-scans sample static tissue. This implies that it is possible to increase adaptively the scan density across the vessels by about a factor of five, when information about the location of the vessel cross-sections is available. A real time adjustment of the scan pattern or scan density can be used to adjust dynamically or adaptively the location and density of samples taken per unit time during an individual scan. The ability will then exist to scan mostly, if not exclusively, the areas of the blood vessels. Another advantage of shorter measurement timescales will be the reduction in deleterious effects of eye movements, which can result in reducing the errors in vessel depth determination which can then alter the vessel's computed orientation. A finer spatial density of scans is thus achievable over blood vessels or other areas of interest.

Difficulty of adequately sampling the heart's pulsation cycle exists given the long-time scale for a single scan to occur. It is an embodiment of this invention, that the scan time of a single scan can be shortened by knowing in advance where the vessels are located, thus Doppler OCT scans can be directed to these specific areas. This directly results in an increased frame rate and, consequently, a higher temporal sampling of the heart's pulsation cycle.

In one embodiment, the positions of the vessels can be detected by one or more fully sampled circumpapillary scan(s). In those scans either the phase data or the intensity data may be used to determine the positions of the blood vessels. Alternatively the vessel locations may also be determined by a full volumetric scan. In this case, the phase data as well as the intensity data may be used to determine the positions of the blood vessels. In both cases the use of retinal tracking may help to improve the precision and repeatability. Alternatively, the vessels may be located by inspection of an image from a fundus camera (such as SLO, LSO, cLSO, or BLFI).

The use of a full volume scan to extract vessel positions also has the advantage to be able to extract the geometric orientation of the blood vessels relative to a probing beam over a larger course of each vessel (see, e.g., Michaely et al. 2007, Singh et al. 2010). Having this information at hand, there is the possibility to direct the scanning beam to the vessel cross sections and, moreover, scan particular regions of each vessel, which exhibit a favorable geometric angle orientation. This avoids measuring vessels at angles approaching orthogonality where the axial (parallel) velocity component is very small. It may, of course, also allow to avoid measuring in very steep regions of the vessels, where the axial velocity component is very high, and thus fringe washout, phase de-correlation, or phase wraps may influence measurement outcomes.

DETAILED DESCRIPTION

Figure 1:
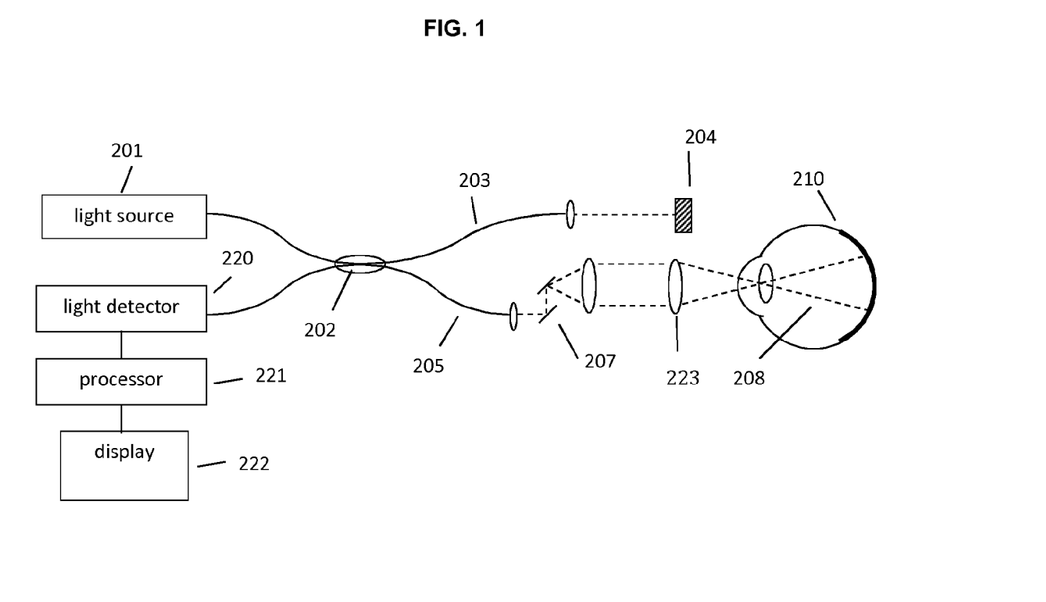
FIG. 1 is a schematic of an optical coherence tomographic instrument based on Fourier-domain technology.

A generalized Fourier Domain optical coherence tomography (FD-OCT) system used to collect an OCT dataset suitable for use with the present set of embodiments, disclosed herein, is illustrated in FIG. 1. A FD-OCT system includes a light source, 201, typical sources including but not limited to broadband light sources with short temporal coherence lengths or swept laser sources.

Light from source (201) is routed, typically by optical fiber (205), to illuminate the sample (210), a typical sample being tissues at the back of the human eye. The light is scanned, typically with a scanner (207) between the output of the fiber and the sample, so that the beam of light or probe beam (dashed line 208) is scanned over the area or volume to be imaged. Light scattered from the sample is collected, typically into the same fiber (205) used to route the light for illumination. Reference light derived from the same source (201) travels a separate path, in this case involving fiber (203) and retro-reflector (204). Those skilled in the art recognize that a transmissive reference path can also be used. Collected sample light is combined with reference light, typically in a fiber coupler (202), to form light interference in a detector (220). The output from the detector is supplied to a processor (221). The results can be stored in the processor (221) or displayed on display (222). The processing and storing functions may be localized within the OCT instrument or functions may be performed on an external processing unit to which the collected data is transferred. This unit could be dedicated to data processing or perform other tasks which are quite general and not dedicated to the OCT device. The display can also provide a user interface for the instrument operator to control the collection and analysis of the data.

The interference causes the intensity of the interfered light to vary across the spectrum. The Fourier transform of the interference light reveals the profile of scattering intensities at different path lengths, and therefore scattering as a function of depth (z-direction) in the sample.

The profile of scattering as a function of depth along the probe beam is called an axial scan (A-scan). A dataset of A-scans measured at neighboring locations in the sample produces a cross-sectional image (slice, tomogram, or B-scan) of the sample. A collection of B-scans collected at different transverse locations on the sample comprises a 3D volumetric dataset. Typically a B-scan is collected along a straight line but B-scans generated from scans of other geometries including circular and spiral patterns are also possible.

The sample and reference arms in the interferometer could consist of bulk-optics, fiber-optics, photonic integrated circuits (PIC) or hybrid bulk-optic systems and could have different architectures such as Michelson, Mach-Zehnder, or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT (time-domain OCT) and SS-OCT systems (swept-source OCT), while spectrometers are typically used at the detection port for SD-OCT (spectral domain OCT) systems. The latter two OCT systems are collectively known as Fourier-domain OCT (FD-OCT). The embodiments described herein could be applied to any type of OCT system.

In one common incorporation of Doppler OCT, one makes use of the easy access to interferometric phase information as a function of depth by the FD-OCT signal reconstruction. This information has per se no absolute value, but the difference of two temporally separated phase measurements at the same location yields an absolute value for small axial motion. For unambiguous velocity determination the phase difference $\Delta\phi$ needs to be confined to $[-\pi, \pi]$:

$$\Delta\Phi = \begin{cases} \Delta\varphi, & |\Delta\varphi| < \pi \\ \Delta\varphi - \text{sign}(\Delta\varphi)2\pi, & |\Delta\varphi| > \pi \end{cases}$$

where $\Delta\Phi$ is the unwrapped phase difference. The axial velocity of a moving scatterer may then be determined by:

$$v = \frac{\lambda}{4\pi\tau}\tan^{-1}\left(\frac{\text{Im}\sum_m \exp(i\Delta\Phi_m)}{\text{Re}\sum_m \exp(i\Delta\Phi_m)}\right)\frac{1}{\cos\alpha},$$

where $\lambda$ is the central wavelength, $\tau$ the time between two measurements, m the number of averaged phase differences, and $\alpha$ is the Doppler angle. The maximum unambiguously quantifiable axial velocity is:

$$v_{max} = \pm\frac{\lambda}{4\tau}.$$

The minimum quantifiable axial velocity is limited by the phase noise $\Phi_{err}$ of the system:

$$v_{min} = \frac{\lambda \Delta \Phi_{err}}{4\pi\tau}.$$

Alternative to the described velocity extraction method, there are other methods described in the literature see, e.g., Szkulmowska et al. 2009, Ren et al. 2002, Y. Wang et al. 2010, R. K. Wang et al. 2009, and Liu et al. 2012. The advantage of the embodiments described in the present application is that they allow for higher temporal resolution circumpapillary scans without increasing phase de-correlation or reducing the sensitivity for lower flow speeds.

In one embodiment of the present application, the basic idea is to increase the frame or acquisition rate of circumpapillary Doppler OCT scans, by dynamically or adaptively adjusting the scan density and location throughout the scan so that the movement of the probe beam in the OCT system between the areas of interest is faster than the movement of the OCT probe beam over the areas of interest. In a system with retinal eye tracking (see, e.g., Ferguson et al. 2004, U.S. Pat. No. 6,325,512, U.S. Pat. No. 6,726,325, U.S. Pat. No. 7,365,856, and US20120249956, all are hereby incorporated by reference) the repeated scans may be locked to the same position on the retina.

Figure 2:
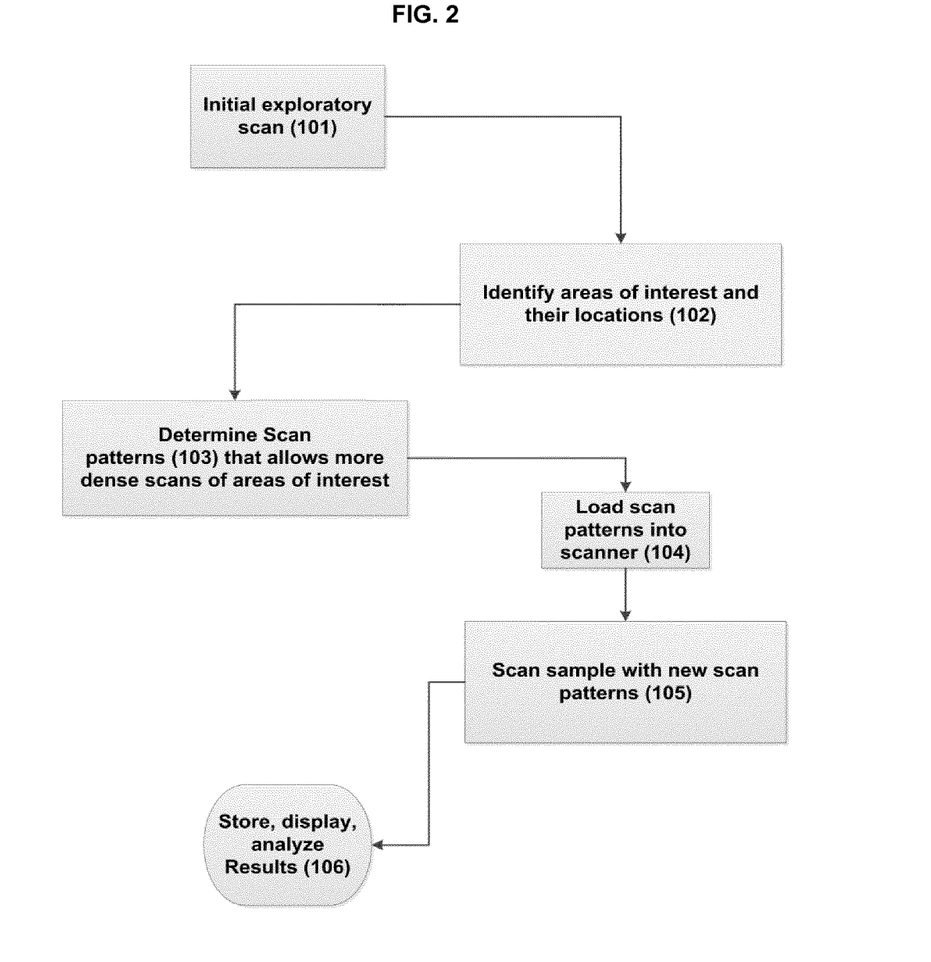
FIG. 2 is a flow chart of one of the embodiments revealed in the present application which services to improve the frame rate of OCT sampling within blood vessels in order to measure flowrate changes due to the cardiac cycle.

This embodiment can be summarized by the flow chart in FIG. 2. An initial exploratory scan (101) with a certain set of scan parameters (integration time, step speed, path, etc.) is conducted and from these data, areas of interest (e.g., blood vessels) are identified (102). The exploratory scan can for example be one or more circumpapillary OCT scan(s), a volume OCT scan or one or more images from a fundus imaging capability such as a fundus camera, LSO (laser scanning ophthalmoscope), SLO (scanning laser ophthalmoscope), BLFI (broad-line fundus imager), or cSLO (confocal SLO), or a combination instrument possessing a fundus imaging capability and an OCT system. (Such systems are described in Bernardes et al. 2011.). Initial locations of areas of interest can be determined (102) from these image data, and, a new set of scan parameters are determined (103) and are then communicated (104) to the scanner (207) and a set of OCT scans then are conducted concentrating on the locations of the areas of interest (105). After acquisition, the results can be stored or displayed or analyzed further (106).

Figure 3:
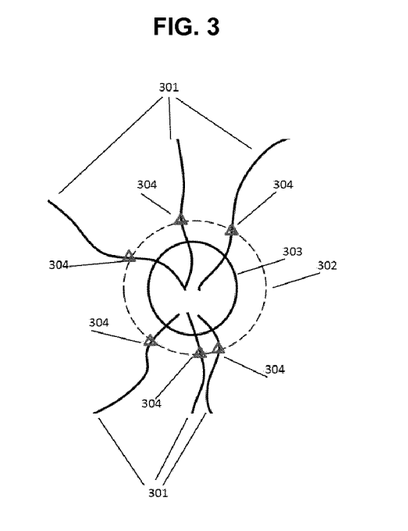
FIG. 3 illustrates a circumpapillary scan (302) with non-linear scanning speed. Triangles (304) indicate densely sampled regions across blood vessels (301). The ad hoc boundary of the ONH is indicated by 303.

Reference is given to FIG. 3, where an exploratory OCT scan (circular or volume) with uniform sampling is performed indicated by dashed circle (302), just outside the limit of the optical nerve head (303). This scan can be used to identify the positions (304) of the vessels (301) on the circle (302) using its phase and/or intensity data (see, e.g., Wang et al. 2008).

Such detection methodologies would be known to the person having ordinary skill in the art.

With this information, additional circular scans (or scans of arbitrary path configuration) can be performed at the same or approximately same locations, but this time, with uneven or non-uniform transverse and/or temporal sampling. In order to increase the frame rate while maintaining dense sampling of the vessels (301), these scans will have denser sampling across the vessels and very sparse or no sampling in the regions where only static tissue is scanned. This can increase the effective frame rate of the circumpapillary scans approximately by a factor of five, resulting in a frame rate of approximately 50 Hz. Such a sampling rate will comprehensively resolve the cardiac cycle even in patients with higher pulse rates and ultimately lead to more precise blood flow measurements.

A similar method can also be used for Doppler OCT non-circumpapillary scans of vessels (401 in FIG. 4), where higher sampling densities are desired for some parts of the scan (404), while other parts of the retina may be scanned less densely (402). The regions to be scanned are chosen due to having more desirable angular relationship to the probe beam (explained below). The limit of the ONH in this figure is indicated as 403.

Such applications could, for example, be an imaging mode, in which parts of a volume scan, containing pathologies (e.g., Srinivasan et al. 2006), are sampled more densely in order to improve image quality in these regions, whereas in other regions of lesser interest, are sampled less densely.

Figure 4:
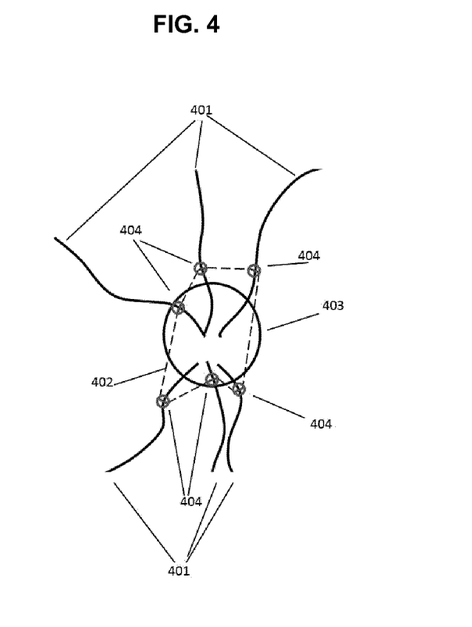
FIG. 4 illustrates an arbitrary scan sampling all vessels (401) entering or exiting the optic nerve head (403). Sampling positions are chosen by a vessel's angle relative to the probing beam in order to optimize the Doppler angle. The dotted lines (402) indicate regions where a scan moves more quickly. Small circles (404) indicate densely-sampled regions across blood vessels.

Another embodiment also contemplated in FIG. 4 would not only make use of prior knowledge of the vessel positions (401), but takes into account the relative geometric orientations of the scan direction with respect to each vessel and position the scan within a region that exhibits a favorable geometric orientation for the measurement. In other words, there should be a choice of a position where there is a preferred geometric orientation that lies within a desired range, and allows an axial velocity measurement with optimal sensitivity. The axial velocity could be considered optimum if it lies well within the minimum measurable velocity, $v_{min}$, and the maximum unambiguously measurable velocity, $v_{max}$.

Figure 5:
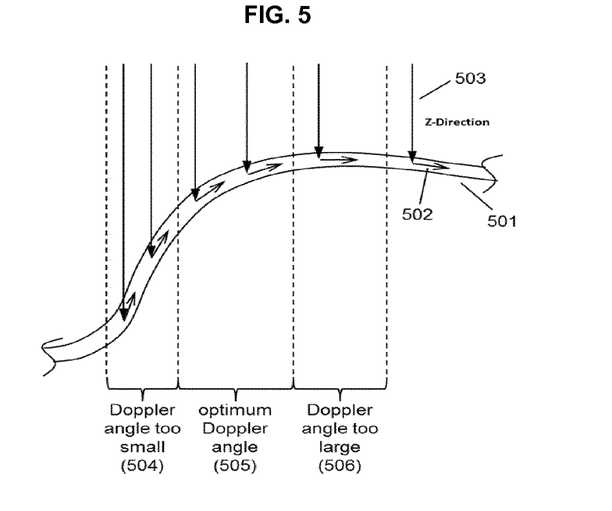
FIG. 5 schematically depicts a lateral view of a blood vessel (501) which varies in depth and one in which the blood flow vector (502) continuously changes as a function of depth (z). With a measurement beam (503) parallel to the vertical, it can be seen in this graphic, that the Doppler angle, which is the angle between flow vector (502) and the direction of the probe beam, will be too small for steep (near parallel) flow (504); optimal when the angle between the blood flow vector (502) and measurement beams are neither close to parallel nor close to perpendicular; and too large when the two vectors (blood flow and probing beam) are essentially orthogonal (506).

FIG. 5 illustrates a side view of a vessel (501) exiting the optic nerve head. This schematic vessel has significant curvature and, therefore, the blood flow velocity vectors (502) have different angles or angular orientations with respect to the probing beam (503). One would like to avoid scanning in regions where the Doppler angles are too small (504) or too large (506). (505) shows a section of the vessel, where the angles between velocity vector and measurement beam lie within a desired range. Since the sections of each vessel do not necessarily lie on a circle, the circumpapillary scan may have an arbitrary shape (FIG. 4). In order to determine the Doppler angle along a range of each vessel, one may, for example, apply methods described by Michaely et al. 2007 or Singh et al. 2010. Because the vessels in the optic nerve head region lie very close to the retinal surface one may alternatively use a topography map, generated from a volumetric scan, to generate a rough estimate of these angles. While these angles determined from the topography map may not be accurate enough to be used for the absolute velocity calculations, they may suffice the requirements of finding suitable scanning regions.

Another embodiment of the present application is to avoid repetitive angle measurements throughout the course of the Doppler OCT measurement. This can be achieved by first measuring the orientations of the vessels of interest with an angle determination method of choice, e.g. double circular scan (see, e.g., Wang et al. 2008; Huang & Wang WO2008124845), reference volume (Singh et al. 2010), vectorial reconstruction (Michaely et al. 2007), and then subsequently monitoring only changes in the orientation of the full sample with respect to the probing beam.

Figure 6:
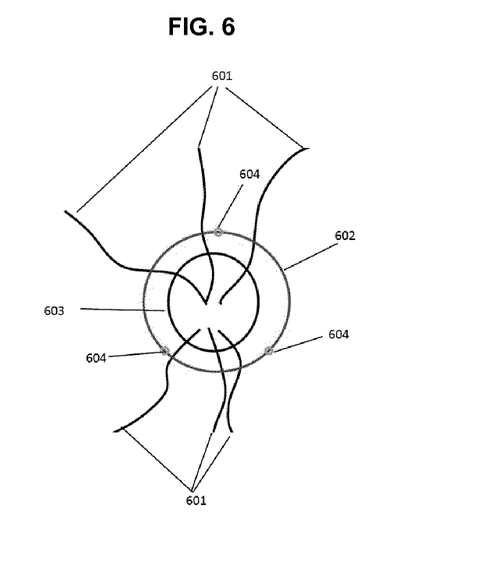
FIG. 6 illustrates a circumpapillary scan (602), where three positions (small circles, 604) are being used for detecting sample orientation changes. The ad hoc boundary of the ONH is indicated by (603). Blood vessels are indicated by (601).

In the case of circumpapillary Doppler OCT scans this approach is straightforward to implement. In FIG. 6, blood vessels are indicated by (601) and (603) is an outline of the ONH. For circular measurements/scans (602) on the retina, there exists the possibility to extract at least three A-scans (604) from the circle and use their depth position for geometric determination of the retina's orientation with respect to the probing beam (via detection of the inner limiting membrane or the retinal pigment epithelium). By performing this geometric analysis continuously for each circumpapillary scan, it is possible to detect changes in the orientation of the retina with respect to the probing beam and is, therefore, also able to quantify changes in the angle between vessel and probing beam.

Figure 7:
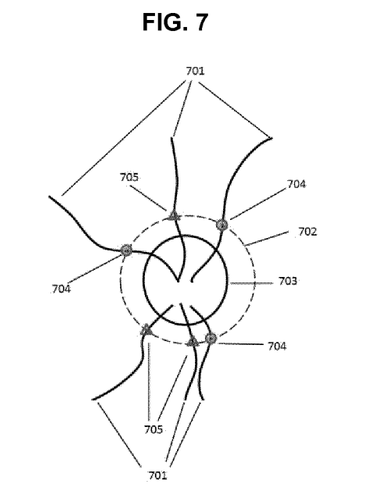
FIG. 7 shows a circumpapillary scan with non-linear scanning speed (702), where three positions (small circles, 704) are being used for detecting sample orientation changes. Blood vessels are indicated by (701). The ad hoc boundary of the ONH is indicated by (703). The triangles (705) and circles (704) are densely-scanned regions.

It is, therefore, no longer required to continuously use a double circular scan pattern. Instead it is sufficient to use only initially a vessel angle determination and then switch to a circular scan pattern with a fixed diameter (FIG. 7, 702). Moreover, the image processing effort is reduced since now only the surface of the retina at three positions of the circular scan has to be detected, which is an easier task in contrast to determining the centers of the vessel's (701) cross sections (704 and 705) in each circular scan.

Figure 8:
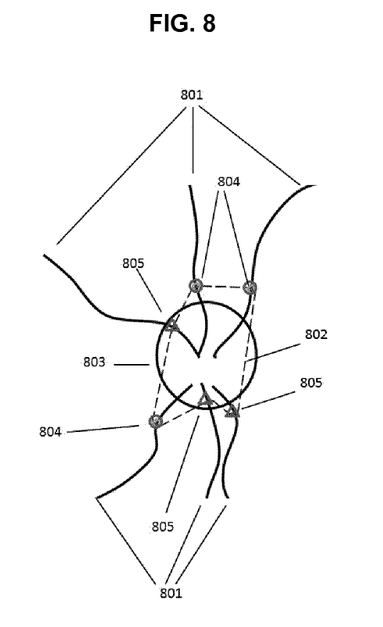
FIG. 8 illustrates an arbitrary scan sampling all vessels (801) entering or exiting the optic nerve head (803), where three positions (804) are analyzed via geometric methods and derive changes in the sample. The triangles (805) and circles (804) are densely-scanned regions.

As depicted in FIG. 8, as long as at least three measurement points (804) are acollinear, their three-dimensional coordinates may be used to determine changes in orientation of the sample between consecutive measurements geometrically. The detected change in sample orientation may be used to update the initially-determined angle of each vessel (805) relative to the measurement beam. The changes in orientation could include tip and tilt or both.

Using the spatial coordinates $(x_i, y_i, z_i, i=1, 2, 3)$ of the three points one can determine the normal vector of the plane, which contains all three measurement points:

$$\vec{n} = \begin{pmatrix} x_2 - x_1 \\ y_2 - y_1 \\ z_2 - z_1 \end{pmatrix} \times \begin{pmatrix} x_3 - x_1 \\ y_3 - y_1 \\ z_3 - z_1 \end{pmatrix}$$

The mathematical operation x is the vector cross product. The normal vector to this plane provides a measure for the orientation of the sample at the time when the original Doppler angles were calculated. In a later measurement one can again use the updated coordinates of the three points to calculate the updated normal vector, which provides a measure for the new orientation of the sample:

$$\vec{n'} = \begin{pmatrix} x'_2 - x'_1 \\ y'_2 - y'_1 \\ z'_2 - z'_1 \end{pmatrix} \times \begin{pmatrix} x'_3 - x'_1 \\ y'_3 - y'_1 \\ z'_3 - z'_1 \end{pmatrix}$$

Since this method is ideally applied with retinal tracking enabled, one can assume that:

$x_i' = x_i$ and $y_i' = y_i$.

One would then normalize the obtained normal vectors:

$$\vec{e_n} = \frac{\vec{n}}{|\vec{n}|}$$

and $$\vec{e_n'} = \frac{\vec{n'}}{|\vec{n'}|}$$

The difference between the two unit vectors then provides a measure of a change of orientation between the first measurement and the second measurement:

$$\Delta \vec{e} = \vec{e_n'} - \vec{e_n}$$

$\Delta \vec{e}$ is then added to each unit velocity vector, which is then used to calculate an updated angle between the updated unit velocity vector and the direction vector of the probing beam.

Figure 9:
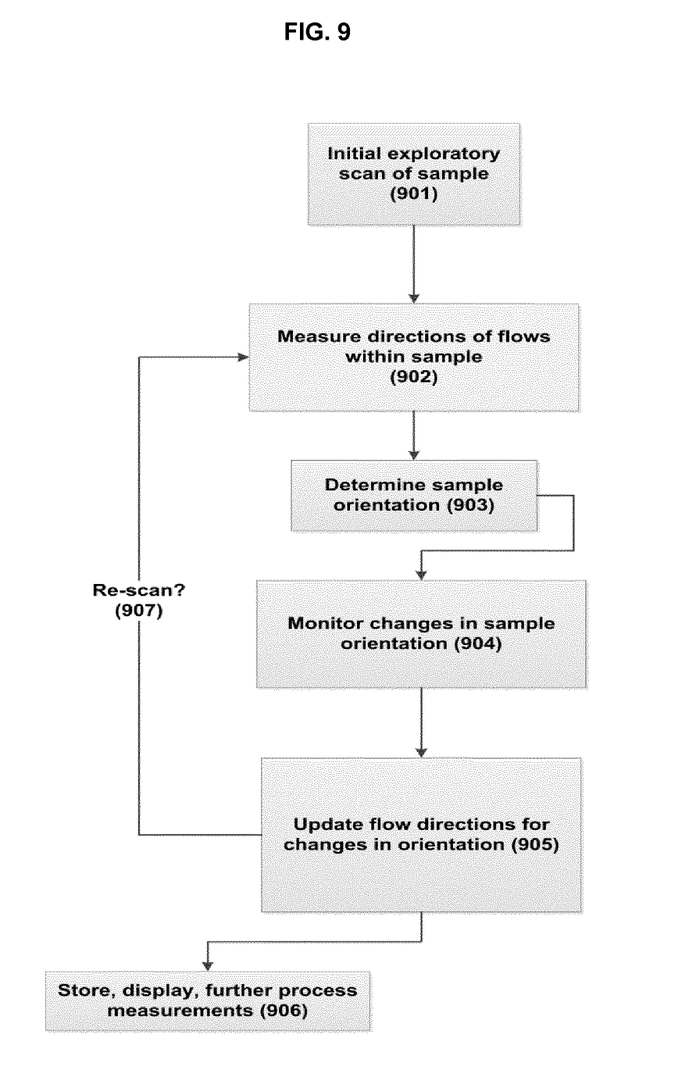
FIG. 9 presents the flow diagram of another embodiment of the present application. It allows the monitoring of orientation changes of a sample due to anatomical movements and the correction of angular measurements, or directions of areas of interest found within the sample.

FIG. 9 presents the basic methodology of this embodiment. An exploratory scan (901) of a sample is (or samples are) conducted and the fluidic flows of interest are located and measured (902). Based upon a favorite algorithm (see above), the directions of the flows are determined (903). From this information, the orientation of the sample (904) relative to the probing beam direction can be derived. The orientation determination could include the angles of tip and tilt relative to the probe beam. The procedure could be used to monitor the orientation changes of the sample (904). The sample orientation is then used to determine the corrections to the flow directions due to anatomical movements (905). The process can be repeated as desired (907). Additional actions, such as further processing, storing, and displaying the results (906) are options. The corrected directions of flows can then be used to determine more accurate flow velocities. An alternative to an exploratory OCT scan is one using images from a fundus imaging capability such as a fundus camera, LSO (laser scanning ophthalmoscope), SLO (scanning laser ophthalmoscope), BLFI (broad-line fundus imager), or cSLO (confocal SLO), or a combination instrument possessing a fundus imaging capability and an OCT system. (Such systems are described in Bernardes et al. 2011.)

The method may also be equally implemented for non-circular scan patterns (FIG. 8). In this embodiment, similar to the aforementioned geometric approach, will consist of a subset of a full scan, and will contain at least three measurements at different locations (804).

If only one vessel is to be evaluated and therefore only measurements at a single location are acquired, one may interleave additional scans for geometric determinations with the regular measurements. Since as few as three A-scans are sufficient for such a geometric measurement, it hardly adds to the total acquisition time. The scans for geometric determination can then be used in the same manner to detect the orientation of the sample and continuously monitor changes in the orientation as was previously described for circular and arbitrary scan patterns (see FIG. 9).

The changes in the orientation of the full sample are again fully applicable to the predetermined angles between probing beam and blood vessel. The areas of interest (805) can then be scanned with a different set of scan parameters. Retinal tracking again helps to improve the accuracy of this method.

Other areas of interest for the monitoring of flow would include the flow and flow rate of aqueous humor in the anterior segment of the eye, or any other fluidic movements within the eye.

The current preferred optical coherence tomography method is Fourier Domain optical coherence tomography, principally due to the faster scan and data rates possible. Thus based upon this modality, it is estimated that scans of blood vessels can occur on the order of at least 25 Hz, which is at the sub-cardiac cycle level, measuring both diastole and systole components, total blood flow, and the presence or absence of any pathologies.

Although various applications and embodiments that incorporate the teachings of the present invention have been shown and described in detail herein, those skilled in the art can readily devise other varied embodiments that still incorporate these teachings.

REFERENCES

The following references are hereby incorporated by reference:

U.S. Pat. No. 6,325,512, U.S. Pat. No. 6,726,325, U.S. Pat. No. 7,365,856, US20120249956

U.S. Pat. No. 8,180,131 Toth et al. "Method, systems and computer program products for mixed-density optical coherence tomography (OCT) imaging"

U.S. Pat. No. 7,884,945 Srinivasan et al. "Methods and apparatus for optical coherence tomography scanning"

US Patent Publication No. 2007/0291277 Everett et al. "Spectral domain optical coherence tomography system"

U.S. Pat. No. 7,365,856 Everett et al. "Method of motion correction in optical coherence tomography imaging"

Chen & Zhang 2008, Doppler Optical Coherence Tomography, in Optical Coherence Tomography, Eds: Drexler and Fujimoto, pp. 621-651, Springer Verlag.

Huang et al. 1991, Optical Coherence Tomography, Science 254 (5035), 1178 1991.

Wang et al. 2008, "In vivo total retinal blood flow measurement by Fourier domain Doppler optical coherence tomography," J. Biomed. Opt. 12, 041215.

Huang & Wang, Methods and systems for blood flow measurement using Doppler optical coherence tomography, WO/2008/124845.

Singh et al. 2010, Stable absolute flow estimation with Doppler OCT based on virtual circumpapillary scans," Biomed. Opt. Express 1, 1047-1059.

Michaely et al. 2007, Vectorial reconstruction of retinal blood flow in three dimensions measured with high resolution resonant Doppler Fourier domain optical coherence tomography, J. Biomed. Opt. 12, 041213.

Liu et al. 2012, A comparison of Doppler optical coherence tomography methods,' Biomed Opt Exp 3(10), 2669-2680.

Tan et al. 2012, Doppler Optical Coherence Tomography of Retinal Circulation, J. Vis. Exp. 67, e3524.

Wang et al. 2008, Retinal Blood flow measurement by circumpapillary fourier domain Doppler optical coherence tomography, J Biomed Opt 13(6), 064003-1 to 9.

Zhao et al. 2000, Doppler standard deviation imaging for clinical monitoring of in vivo human skin blood flow, Opt Lett 25(18), 1358-1360.

Ferguson et al. 2004, Tracking Optical Coherence Tomography, Opt. Lett. 29, 2139-2141.

Srinivasan et al. 2006, High-definition and 3-dimensional imaging of macular pathologies with high-speed ultra-high-resolution optical coherence tomography, Ophthalmology 113, 2054-2065.

Szkulmowska et al. 2009, Three-dimensional quantitative imaging of the retinal and choroidal blood flow velocity using joint Spectral and Time domain Optical Coherence Tomography, Opt Exp 17, 10584-10598.

Y. Wang et al. 2010, Autocorrelation optical coherence tomography for mapping transverse particle-flow velocity, Opt. Lett. 35, 3538-3540, 2010

R. K. Wang et al. 2009, Doppler optical micro-angiography for volumetric imaging of vascular perfusion in vivo, Opt. Exp 17, 8926.

Park et al. 2005, Real-time fiber-based multi-functional spectral-domain optical coherence tomography at 1.3 µm, Opt. Exp 13, 3931-3944.

Bernardes et al. 2001, Ophthalmologica 226(4), 161-181.

The invention claimed is:

1. A method of determining blood flow in the vessels in a retina of an eye based on measurements obtained from an optical coherence tomography (OCT) system, said system including a scanner for scanning a measurement beam across the eye, said method comprising the steps of:
generating an image of the retina;
determining the location and angular orientation of blood vessels within the image and identifying sections of the vessels having an angular orientation with respect to the scanning beam where the velocity of moving scatterers inside the vessels is best measured;
obtaining a set of Doppler OCT measurements by scanning the beam over the identified sections of the blood vessels;
determining the velocity of moving scatterers in the vessels based on the Doppler OCT measurements; and
displaying or storing information of the determined velocity.

2. A method as recited in claim 1, wherein the determined velocity information is used to calculate the blood flow in the vessels.

3. A method as recited in claim 1, wherein the image of the retina is generated with a fundus camera.

4. A method as recited in claim 1, wherein the image of the retina is generated by measurements made by the OCT system by scanning the beam over the retina.

5. A method as recited in claim 4, wherein the spatial density of the Doppler OCT measurements is higher than the spatial density of the measurements used to generate the image of the retina.

6. A method as recited in claim 4, wherein the spatial density of the Doppler OCT measurements is higher across the blood vessels than the spatial density of Doppler OCT measurements in between the blood vessels.

7. A method as recited in claim 1, wherein during the step of obtaining a set of Doppler OCT measurements by scanning the beam in the identified sections of the blood vessels, measurements are obtained to determine any changes to the orientation of the retina, said determination being used to update the previously determined location and orientation of the blood vessels.

8. A method as recited in claim 1, wherein the step of obtaining a set of Doppler OCT measurements includes obtaining temporally separated phase measurements at the same location in the retina.

9. A method as recited in claim 8, wherein the step of determining the velocity of moving scatterers in the vessels includes comparing the difference in the phase measurements obtained at the same location in the retina.

10. A method as recited in claim 1, wherein the Doppler OCT measurements are based on one of the following methods: phase difference Doppler OCT, phase-resolved Doppler variance, intensity-based Doppler variance, joint spectral and time domain OCT, optical microangiograpy, Doppler optical microangiography, bidirectional Doppler OCT, three-beam Doppler OCT.

11. A method as recited in claim 1, wherein the identified sections of the blood vessel have an angular orientation lower than a predetermined high limit and higher than a predetermined low limit.

12. A method for obtaining blood flow measurements within blood vessels in the retina of an eye using an optical coherence tomography (OCT) system including a scanner for scanning a measurement beam across the eye, said method comprising the steps of:
  obtaining a first set of measurements by scanning the beam over the retina;
  generating an image of the retina based on the first measurements;
  determining the location and angular orientation of blood vessels within the image;
  obtaining a set of Doppler OCT measurements by scanning the beam over the blood vessels based on the determined locations and angular orientations thereof;
  while obtaining the set of Doppler OCT measurements, periodically determining the changes in the orientation of the retina, with the determination being used to update the previously determined location and orientation of the blood vessels;
  determining the velocity of moving scatterers in the vessels based on the Doppler OCT measurements; and
  displaying or storing the information of the determined velocity.

13. A method as recited in claim 12, wherein the step of periodically determining the changes in the orientation of the retina includes acquiring three or more A-scans of the retina that are non-collinear.

14. A method as recited in claim 12, wherein the step of periodically determining the changes in the orientation of the retina includes extracting three or more A-scans from the Doppler OCT measurements that are non-collinear.

15. A method as recited in claim 14, wherein the acquired A-scans are used to detect the location of the inner limiting membrane of the retina.

16. A method as recited in claim 14, wherein the acquired A-scans are used to detect the location of the retinal pigment epithelium of the retina.

17. A method as recited in claim 12, wherein the determined velocity information is used to calculate the blood flow in the vessels.

* * * * *

UNITED STATES PATENT AND TRADEMARK OFFICE
CERTIFICATE OF CORRECTION

PATENT NO. : 9,814,384 B2
APPLICATION NO. : 15/021770
DATED : November 14, 2017
INVENTOR(S) : Tilman Schmoll Page 1 of 1

It is certified that error appears in the above-identified patent and that said Letters Patent is hereby corrected as shown below:

In the Specification

In Column 4, Line 32, delete "cLSO," and insert -- cSLO, --, therefor.

In Column 9, Line 35, delete "x" and insert -- × --, therefor.

In the Claims

In Column 12, Line 59, in Claim 10, delete "microangiograpy," and insert -- microangiography, --, therefor.

In Column 14, Line 1, in Claim 12, before "information" delete "the".

Signed and Sealed this
Twentieth Day of February, 2018

Andrei Iancu
*Director of the United States Patent and Trademark Office*